US008992486B2

(12) United States Patent
Veasey et al.

(10) Patent No.: US 8,992,486 B2
(45) Date of Patent: Mar. 31, 2015

(54) PEN-TYPE INJECTOR

(71) Applicants: Robert Frederick Veasey, Warwickshire (GB); Robert Perkins, Oxfordshire (GB); David Aubrey Plumptre, Worcestershire (GB)

(72) Inventors: Robert Frederick Veasey, Warwickshire (GB); Robert Perkins, Oxfordshire (GB); David Aubrey Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 95 days.

(21) Appl. No.: 13/909,681

(22) Filed: Jun. 4, 2013

(65) Prior Publication Data
US 2013/0267906 A1    Oct. 10, 2013

Related U.S. Application Data

(63) Continuation of application No. 12/944,544, filed on Nov. 11, 2010, now Pat. No. 8,679,069, which is a continuation of application No. 11/483,546, filed on Jul. 11, 2006, now Pat. No. 7,918,833, which is a continuation of application No. 10/790,225, filed on Mar. 2, 2004, now abandoned.

(30) Foreign Application Priority Data

Mar. 3, 2003  (GB) .................................. 0304822.0

(51) Int. Cl.
*A61M 5/00* (2006.01)
*A61M 5/315* (2006.01)
*A61M 5/24* (2006.01)

(52) U.S. Cl.
CPC ............. *A61M 5/31533* (2013.01); *A61M 5/24* (2013.01); *A61M 5/31535* (2013.01);
(Continued)

(58) Field of Classification Search
CPC ..................... A61M 5/31533; A61M 5/31536; A61M 5/31535; A61M 5/31551; A61M 5/31541; A61M 5/31585
USPC .......... 604/187, 207–211, 218, 221, 224, 232
See application file for complete search history.

(56) References Cited

U.S. PATENT DOCUMENTS 5,304,152 A    4/1994  Sams
5,320,609 A    6/1994  Haber et al.
(Continued)

FOREIGN PATENT DOCUMENTS

EP    0937471 A2    8/1999
EP    0937476 A2    8/1999
(Continued)

*Primary Examiner* — Manuel Mendez
(74) *Attorney, Agent, or Firm* — McDonnell Boehnen Hulbert & Berghoff LLP

(57) ABSTRACT

A housing for a dispensing apparatus. The housing comprising a main housing and a dose dial sleeve. The dose dial sleeve comprising a helical groove configured to engage a threading provided by the housing. A dose knob is disposed near a proximal end of the dose dial sleeve and a piston rod is provided within the housing. The piston rod is non-rotatable during a dose setting step. A driver comprises an internal threading near a distal portion of the driver and is adapted to engage an external thread of the piston rod. A tubular clutch is located adjacent a distal end of the dose knob and operatively coupled to the dose knob. The dose dial sleeve may extend circumferentially around at least a portion of the tubular clutch.

57 Claims, 7 Drawing Sheets

(52) U.S. Cl.
CPC ...... *A61M 5/31541* (2013.01); *A61M 5/31551* (2013.01); *A61M 5/3156* (2013.01); *A61M 5/31575* (2013.01); *A61M 5/31585* (2013.01); *A61M 2005/2407* (2013.01); *A61M 2205/581* (2013.01); *A61M 2205/582* (2013.01); *A61M 5/31536* (2013.01)
USPC .......................................................... 604/209

(56) References Cited

U.S. PATENT DOCUMENTS

| | | |
|---|---|---|
| 5,480,387 A | 1/1996 | Gabriel et al. |
| 5,505,704 A | 4/1996 | Pawelka et al. |
| 5,626,566 A | 5/1997 | Petersen et al. |
| 5,674,204 A | 10/1997 | Chanoch |
| 5,688,251 A | 11/1997 | Chanoch |
| 6,083,197 A | 7/2000 | Umbaugh |
| 6,193,698 B1 | 2/2001 | Kirchhofer et al. |
| 6,221,046 B1 | 4/2001 | Burroughs et al. |
| 6,248,095 B1 | 6/2001 | Giambattista et al. |
| 6,899,698 B2 | 5/2005 | Sams |
| 7,241,278 B2 | 7/2007 | Moller |
| 8,679,069 B2 * | 3/2014 | Veasey et al. .................. 604/209 |
| 2002/0052578 A1 | 5/2002 | Moller |
| 2004/0059299 A1 | 3/2004 | Moller et al. |

FOREIGN PATENT DOCUMENTS

| | | |
|---|---|---|
| WO | 91/14467 A1 | 10/1991 |
| WO | 99/38554 A1 | 8/1999 |
| WO | 9938554 A1 | 8/1999 |

* cited by examiner

PEN-TYPE INJECTOR

CROSS REFERENCE TO RELATED APPLICATIONS

The present application is a continuation application of U.S. patent application Ser. No. 12/944,544, filed Nov. 11, 2010, entitled "Pen-Type Injector", which is a continuation application of U.S. patent application Ser. No. 11/483,546, filed Jul. 11, 2006, now U.S. Pat. No. 7,918,833, which is a continuation application of U.S. patent application Ser. No. 10/790,225, filed Mar. 2, 2004, abandoned, and claims priority to GB Patent Application No. 0304822.0, filed Mar. 3, 2003, the entire contents of each of which are incorporated herein by reference.

BACKGROUND

Improvements in and Relating to a Pen-Type Injector

The present invention relates to pen-type injectors, that is to injectors of the kind that provide for administration by injection of medicinal products from a multidose cartridge. In particular, the present invention relates to such injectors where a user may set the dose.

Such injectors have application where regular injection by persons without formal medical training occurs. This is increasingly common amongst those having diabetes where self-treatment enables such persons to conduct effective management of their diabetes.

These circumstances set a number of requirements for pen-type injectors of this kind. The injector must be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of (preferably being suitable for recycling).

Overview

It is an advantage of the present invention that an improved pen-type injector is provided.

According to a first aspect of the present invention, a pen-type injector comprises a housing;
  a piston rod adapted to operate through the housing;
  a dose dial sleeve located between the housing and the piston rod, the dose dial sleeve having a helical thread of first lead;
  a drive sleeve located between the dose dial sleeve and the piston rod, the drive sleeve having a helical groove of second lead;
  characterized in that the first lead of the helical thread and the second lead of the helical groove are the same.

Preferably, the piston rod has a first threaded portion at a first end and a second threaded portion at a second end;
  an insert or radially inwardly extending flange is located in the housing and through which the first threaded portion of the piston rod may rotate;
  the dose dial sleeve being rotatable with respect to the housing and the insert;
  the drive sleeve being releasably connected to the dose dial sleeve and connected to the piston rod for rotation with respect thereto along the second threaded portion of the piston rod;
  a button is located on the dose dial sleeve and rotatable with respect to the dose dial sleeve; and
  clutch means are provided which upon depression of the button permit rotation between the dose dial sleeve and the drive sleeve.

Preferably, the injector further comprises a nut which is rotatable with respect to the drive sleeve and axially displaceable but not rotatable with respect to the housing.

More preferably, the drive sleeve is provided at a first end with first and second flanges with an intermediate thread between the first and second flanges, the nut being disposed between the first and second flanges and keyed to the housing by spline means. Additionally, a first radial stop may be provided on a second face of the nut and a second radial stop may be provided on a first face of the second flange.

Preferably, the first thread of the piston rod is oppositely disposed to the second thread of the piston rod.

Preferably, a second end of the clutch is provided with a plurality of dog teeth adapted to engage with a second end of the dose dial sleeve.

Preferably, the pen-type injector further includes clicker means disposed between the clutch means and spline means provided on the housing.

More preferably, the clicker means comprises a sleeve provided at a first end with a helically extending arm, a free end of the arm having a toothed member, and at a second end with a plurality of circumferentially directed saw teeth adapted to engage a corresponding plurality of circumferentially saw teeth provided on the clutch means.

Alternatively, the clicker means comprises a sleeve provided at a first end with at least one helically extending arm and at least one spring member, a free end of the arm having a toothed member, and at a second end with a plurality of circumferentially directed saw teeth adapted to engage a corresponding plurality of circumferentially directed saw teeth provided on the clutch means.

Preferably, the main housing is provided with a plurality of maximum dose stops adapted to be abutted by a radial stop provided on the dose dial sleeve. More preferably, at least one of the maximum dose stops comprises a radial stop located between a helical rib and spline means provided at a second end of the housing. Alternatively, at least one of the maximum dose stops comprises a part of a raised window portion provided at a second end of the housing.

Preferably, the dose dial sleeve is provided with a plurality of radially extending members adapted to abut a corresponding plurality of radial stops provided at a second end of the housing.

BRIEF DESCRIPTION OF THE DRAWINGS

The invention will now be described with reference to the accompanying drawings, in which:—

DETAILED DESCRIPTION

Figures 1, 2:
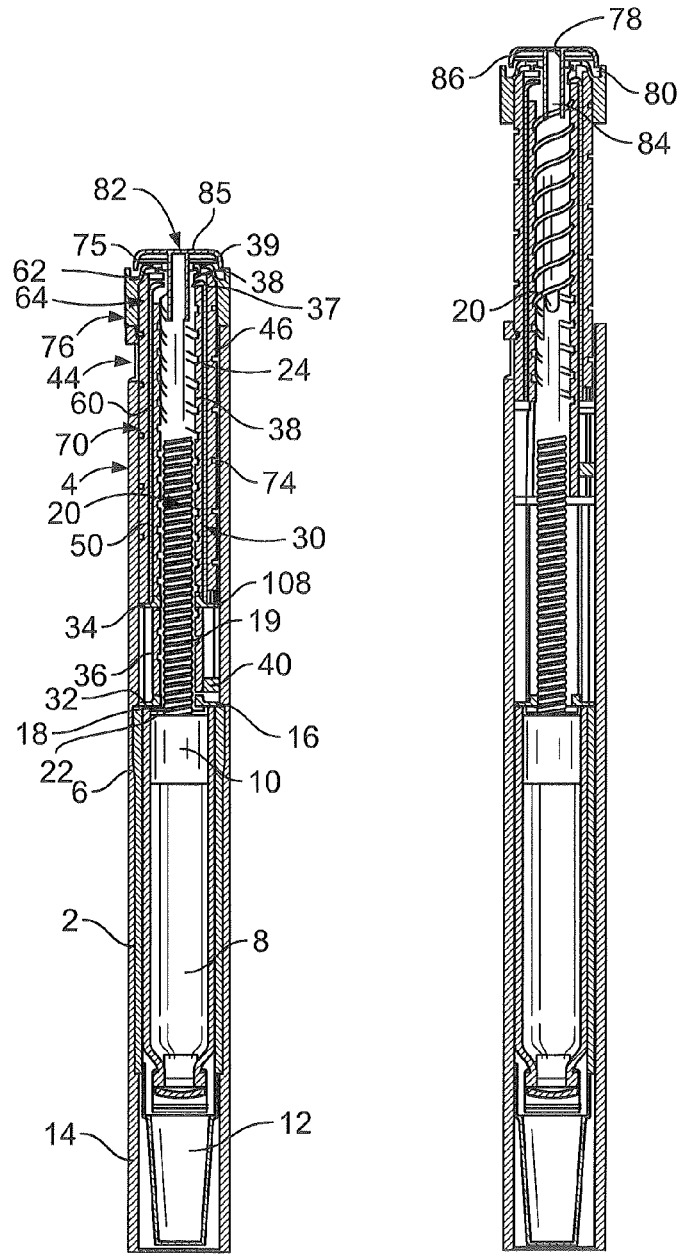
FIG. 1 shows a sectional view of a pen-type injector in accordance with the present invention in a first, cartridge full, position.
FIG. 2 shows a sectional view of the pen-type injector of FIG. 1 in a second, maximum first dose dialed, position.
Figures 3, 4:
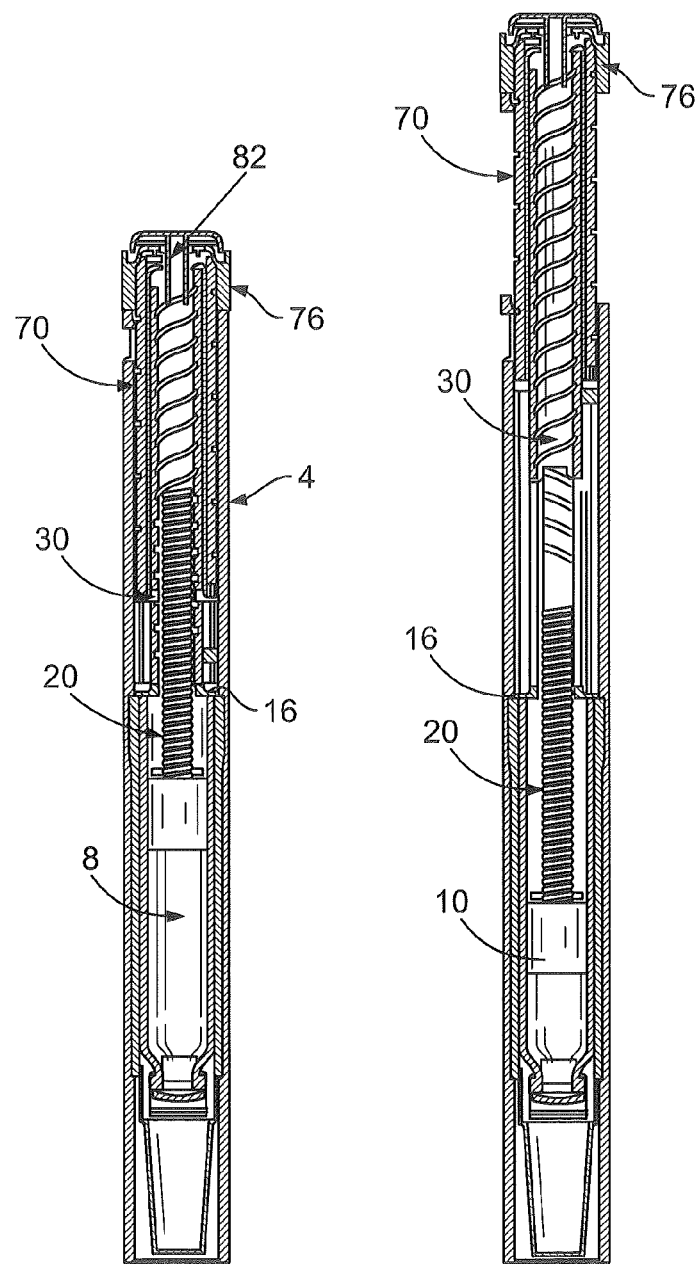
FIG. 3 shows a sectional view of the pen-type injector of FIG. 1 in a third, first maximum first dose dispensed, position.
FIG. 4 shows a sectional view of the pen-type injector of FIG. 1 in a fourth, final dose dialed, position.
Figure 5:
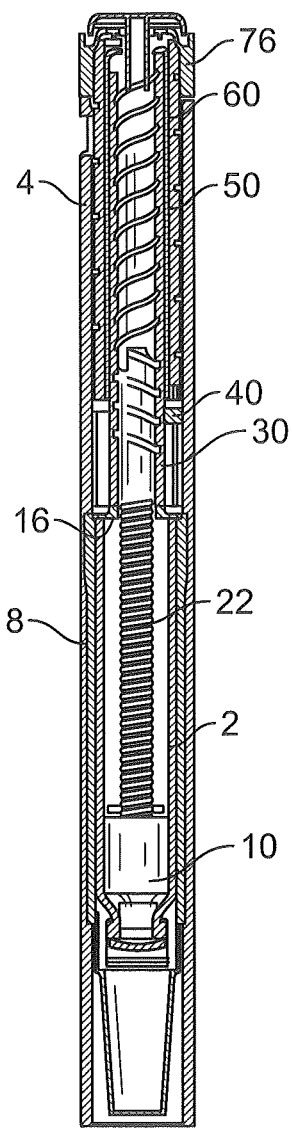
FIG. 5 shows a sectional view of the pen-type injector of FIG. 1 in a fifth, final dose dispensed, position.

Referring first to FIGS. 1 to 5, there may be seen a pen-type injector in accordance with the present invention in a number of positions.

The pen-type injector comprises a housing having a first cartridge retaining part 2, and second main housing part 4. A first end of the cartridge retaining means 2 and a second end of the main housing 4 are secured together by retaining features 6. In the illustrated embodiment, the cartridge retaining means 2 is secured within the second end of the main housing 4.

A cartridge 8 from which a number of doses of medicinal product may be dispensed is provided in the cartridge retaining part 2. A piston 10 is retained in a first end of the cartridge 8.

A removable cap 12 is releasably retained over a second end of the cartridge retaining part 2. In use the removable cap 12 can be replaced by a user with a suitable needle unit (not shown). A replacable cap 14 is used to cover the cartridge retaining part 2 extending from the main housing 4. Preferably, the outer dimensions of the replaceable cap 14 are similar or identical to the outer dimensions of the main housing 4 to provide the impression of a unitary whole when the replaceable cap 14 is in position covering the cartridge retaining part 2.

In the illustrated embodiment, an insert 16 is provided at a first end of the main housing 4. The insert 16 is secured against rotational or longitudinal motion. The insert 16 is provided with a threaded circular opening 18 extending therethrough. Alternatively, the insert may be formed integrally with the main housing 4 the form of a radially inwardly directed flange having an internal thread.

A first thread 19 extends from a first end of a piston rod 20. The piston rod 20 is of generally circular section. The first end of the piston rod 20 extends through the threaded opening 18 in the insert 16. A pressure foot 22 is located at the first end of the piston rod 20. The pressure foot 22 is disposed to abut a second end of the cartridge piston 10. A second thread 24 extends from a second end of the piston rod 20. In the illustrated embodiment the second thread 24 comprises a series of part threads rather than a complete thread. The illustrated embodiment is easier to manufacture and helps reduce the overall force required for a user to cause medicinal product to be dispensed.

The first thread 19 and the second thread 24 are oppositely disposed. The second end of the piston rod 20 is provided with a receiving recess 26.

A drive sleeve 30 extends about the piston rod 20. The drive sleeve 30 is generally cylindrical. The drive sleeve 30 is provided at a first end with a first radially extending flange 32. A second radially extending flange 34 is provided spaced a distance along the drive sleeve 30 from the first flange 32. An intermediate thread 36 is provided on an outer part of the drive sleeve 30 extending between the first flange 32 and the second flange 34. A helical groove 38 extends along the internal surface of the drive sleeve 30. The second thread 24 of the piston rod 20 is adapted to work within the helical groove 38.

A first end of the first flange 32 is adapted to conform to a second side of the insert 16.

A nut 40 is located between the drive sleeve 30 and the main housing 2, disposed between the first flange 32 and the second flange 34. In the illustrated embodiment the nut 40 is a half-nut. This assists in the assembly of the injector. The nut 40 has an internal thread matching the intermediate thread 36. The outer surface of the nut 40 and an internal surface of the main housing 4 are keyed together by splines 42 (see FIGS. 10, 11, 15 and 16) to prevent relative rotation between the nut 40 and the main housing 4, while allowing relative longitudinal movement therebetween.

A shoulder 37 is formed between a second end of the drive sleeve 30 and an extension 38 provided at the second end of the drive sleeve 30. The extension 38 has reduced inner and outer diameters in comparison to the remainder of the drive sleeve 30. A second end of the extension 38 is provided with a radially outwardly directed flange 39.

A clicker 50 and a clutch 60 are disposed about the drive sleeve 30, between the drive sleeve 30 and a dose dial sleeve 70 (to be described below).

Figure 6:
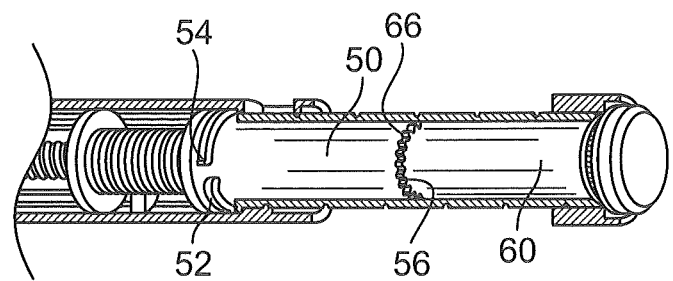
FIG. 6 shows a cut-away view of a first detail of the pen-type injector of FIG. 1.

The clicker 50 is located adjacent the second flange 34 of the drive sleeve 30. The clicker 50 is generally cylindrical and is provided at a first end with a flexible helically extending arm 52 (shown most clearly in FIG. 6). A free end of the arm 52 is provided with a radially directed toothed member 54. A second end of the clicker 50 is provided with a series of circumferentially directed saw teeth 56 (cf FIG. 7). Each saw tooth comprises a longitudinally directed surface and an inclined surface.

In an alternative embodiment (not shown) the clicker means further includes at least one spring member. The at least one spring member assists in the resetting of the clutch means 60 following dispense.

The clutch means 60 is located adjacent the second end of the drive sleeve 30. The clutch means 60 is generally cylindrical and is provided at a first end with a series of circumferentially directed saw teeth 66 (see FIG. 7). Each saw tooth comprises a longitudinally directed surface and an inclined surface. Towards the second end 64 of the clutch means 60 there is located a radially inwardly directed flange 62. The flange 62 of the clutch means 60 is disposed between the shoulder 37 of the drive sleeve 30 and the radially outwardly directed flange 39 of the extension 38. The second end of the clutch means 60 is provided with a plurality of dog teeth 65 (FIG. 8). The clutch 60 is keyed to the drive sleeve 30 by way of splines (not shown) to prevent relative rotation between the clutch 60 and the drive sleeve 30.

In the illustrated embodiment, the clicker 50 and the clutch 60 each extend approximately half the length of the drive sleeve 30. However, it will be understood that other arrangements regarding the relative lengths of these parts are possible.

Figure 7:
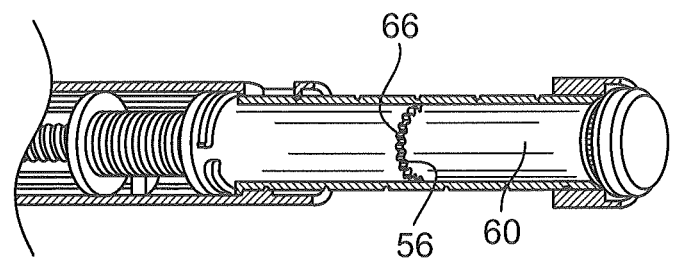
FIG. 7 shows a partially cut-away view of a second detail of the pen-type injector of FIG. 1.
Figure 8:
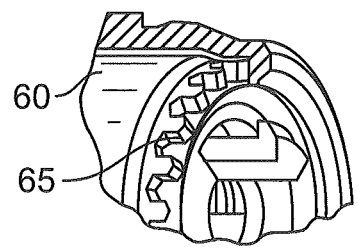
FIG. 8 shows a partially cut-away view of a third detail of the pen-type injector of FIG. 1.

The clicker 50 and the clutch means 60 are normally engaged, that is as shown in FIG. 7.

A dose dial sleeve 70 is provided outside of the clicker 50 and clutch means 60 and radially inward of the main housing 4. A helical groove 74 is provided about an outer surface of the dose dial sleeve 70.

Figure 15:
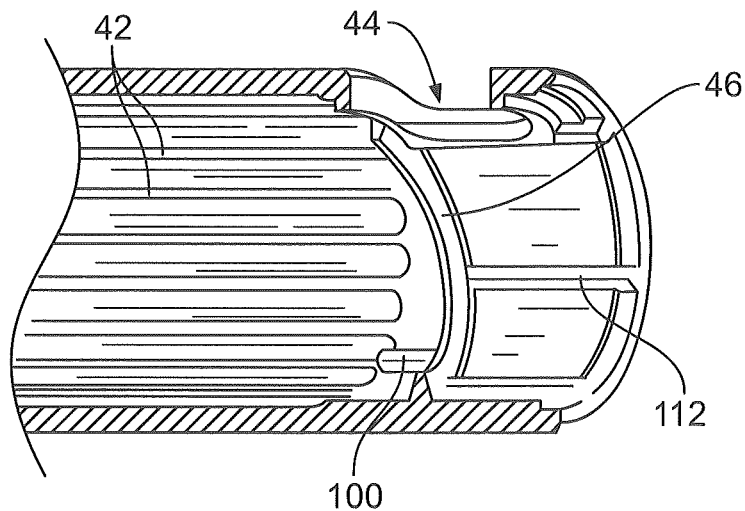
FIG. 15 shows a cut-away view of a first part of a main housing of the pen-type injector of FIG. 1.
Figure 16:
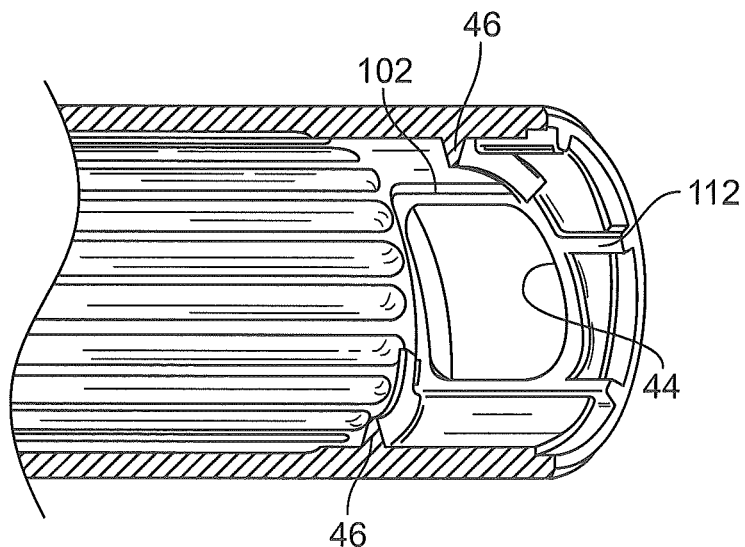
FIG. 16 shows a cut-away view of a second part of the main housing of the pen-type injector of FIG. 1.

The main housing 4 is provided with a window 44 through which a part of the outer surface of the dose dial sleeve may be seen. The main housing 4 is further provided with a helical rib 46, adapted to be seated in the helical groove 74 on the outer surface of the dose dial sleeve 70. The helical rib 46 extends for a single sweep of the inner surface of the main housing 4. A first stop 100 is provided between the splines 42 and the helical rib 46 (FIG. 15). A second stop 102, disposed at an angle of 180° to the first stop 100 is formed by a frame surrounding the window 44 in the main housing 4 (FIG. 16).

Conveniently, a visual indication of the dose that may be dialed, for example reference numerals (not shown), is provided on the outer surface of the dose dial sleeve 70. The window 44 conveniently only allows to be viewed a visual indication of the dose currently dialed.

A second end of the dose dial sleeve 70 is provided with an inwardly directed flange in the form of number of radially extending members 75. A dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement therebetween. The dose dial grip 76 is provided with a central opening 78. An annular recess 80 located in the second end of the dose dial grip 76 extends around the opening 78.

A button 82 of generally 'T' section is provided at a second end of the pen-type injector. A stem 84 of the button 82 may extend through the opening 78 in the dose dial grip 76, through the inner diameter of the extension 38 of the drive sleeve 30 and into the receiving recess 26 of the piston rod 20. The stem 84 is retained for limited axial movement in the drive sleeve 30 and against rotation with respect thereto. A head 85 of the button 82 is generally circular. A skirt 86 depends from a periphery of the head 85. The skirt 86 is adapted to be seated in the annular recess 80 of the dose dial grip 76.

Figure 9:
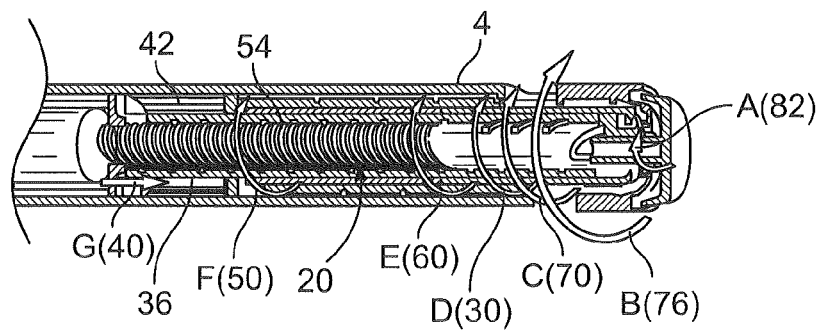
FIG. 9 shows the relative movement of parts of the pen-type injector shown in FIG. 1 during dialing up of a dose.
Figure 10:
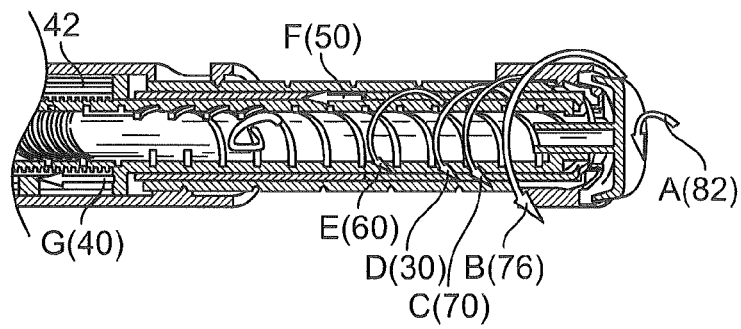
FIG. 10 shows the relative movement of parts of the pen-type injector shown in FIG. 1 during dialing down of a dose.
Figure 11:
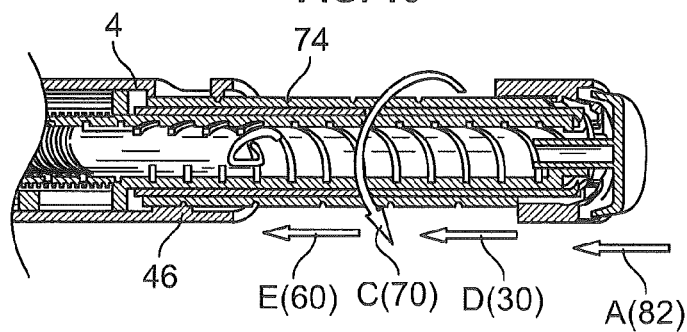
FIG. 11 shows the relative movement of parts of the pen-type injector shown in FIG. 1 during dispensing of a dose.
Figure 12:
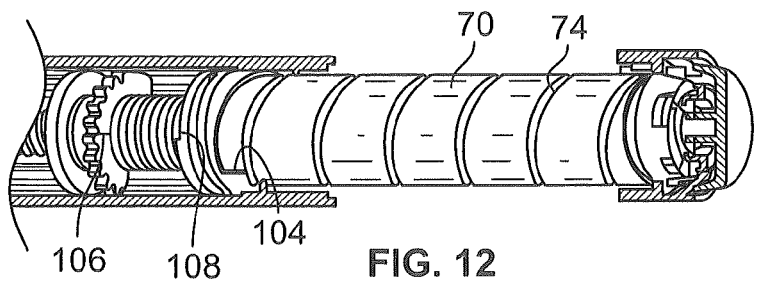
FIG. 12 shows a partially cut-away view of the pen-type injector of FIG. 1 in the second, maximum first dose dialed, position.

Operation of the pen-type injector in accordance with the present invention will now be described. In FIGS. 9, 10 and 11 arrows A, B, C, D, E, F and G represent the respective movements of the button 82, the dose dial grip 76, the dose dial sleeve 70, the drive sleeve 30, the clutch means 60, the clicker 50 and the nut 40.

To dial a dose (FIG. 9) a user rotates the dose dial grip 76 (arrow A). With the clicker 50 and clutch means 60 engaged, the drive sleeve 30, the clicker 50, the clutch means 60 and the dose dial sleeve 70 rotate with the dose dial grip 76.

Audible and tactile feedback of the dose being dialed is provided by the clicker 50 and the clutch means 60. Torque is transmitted through the saw teeth 56,66 between the clicker 50 and the clutch means 60. The flexible arm 52 deforms and drags the toothed member 54 over the splines 42 to produce a click. Preferably, the splines 42 are disposed such that each click corresponds to a unit dose.

The helical groove 74 on the dose dial sleeve 70 and the helical groove 38 in the drive sleeve 30 have the same lead. This allows the dose dial sleeve 70 (arrow C) to extend from the main housing 4 and the drive sleeve 30 (arrow D) to climb the piston rod 20 at the same rate. At the limit of travel, a radial stop 104 on the dose dial sleeve 70 engages either the first stop 100 or the second stop 102 provided on the main housing 4 to prevent further movement. Rotation of the piston rod 20 is prevented due to the opposing directions of the overhauled and driven threads on the piston rod 20.

Figure 13:
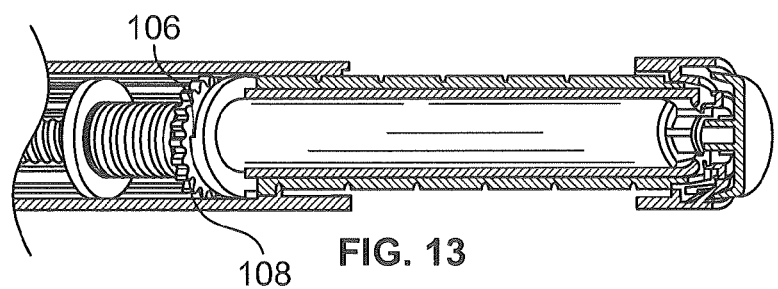
FIG. 13 shows a partially cut-away view of the pen-type injector of FIG. 1 in the fourth, final dose dialed, position.

The nut 40, keyed to the main housing 4, is advanced along the intermediate thread 36 by the rotation of the drive sleeve 30 (arrow D). When the final dose dispensed position (FIGS. 4, 5 and 13) is reached, a radial stop 106 formed on a second surface of the nut 40 abuts a radial stop 108 on a first surface of the second flange 34 of the drive sleeve 30, preventing both the nut 40 and the drive sleeve 30 from rotating further.

In an alternative embodiment (not shown) a first surface of the nut 40 is provided with a radial stop for abutment with a radial stop provided on a second surface of the first flange 32. This aids location of the nut 40 at the cartridge full position during assembly of the pen-type injector.

Should a user inadvertently dial beyond the desired dosage, the pen-type injector allows the dosage to be dialed down without dispense of medicinal product from the cartridge (FIG. 10). The dose dial grip 76 is counter rotated. This causes the system to act in reverse. The flexible arm 52 now acts as a ratchet preventing the clicker from rotating. The torque transmitted through the clutch means 60 causes the saw teeth 56, 66 to ride over one another to create the clicks corresponding to dialed dose reduction. Preferable the saw teeth 56, 66 are so disposed that the circumferential extent of each saw tooth corresponds to a unit dose.

When the desired dose has been dialed, the user may then dispense this dose by depressing the button 82 (FIG. 11). This displaces the clutch means 60 axially with respect to the dose dial sleeve 70 causing the dog teeth 65 to disengage. However the clutch means 60 remains keyed in rotation to the drive sleeve 30. The dose dial sleeve 70 and associated dose dial grip 76 are now free to rotate (guided by the helical rib 46 located in helical groove 74).

The axial movement deforms the flexible arm 52 of the clicker 50 to ensure the saw teeth 56,66 cannot be overhauled during dispense. This prevents the drive sleeve 30 from rotating with respect to the main housing 4 though it is still free to move axially with respect thereto. This deformation is subsequently used to urge the clicker 50, and the clutch 60, back along the drive sleeve 30 to restore the connection between the clutch 60 and the dose dial sleeve 70 when pressure is removed from the button 82.

Figure 14:
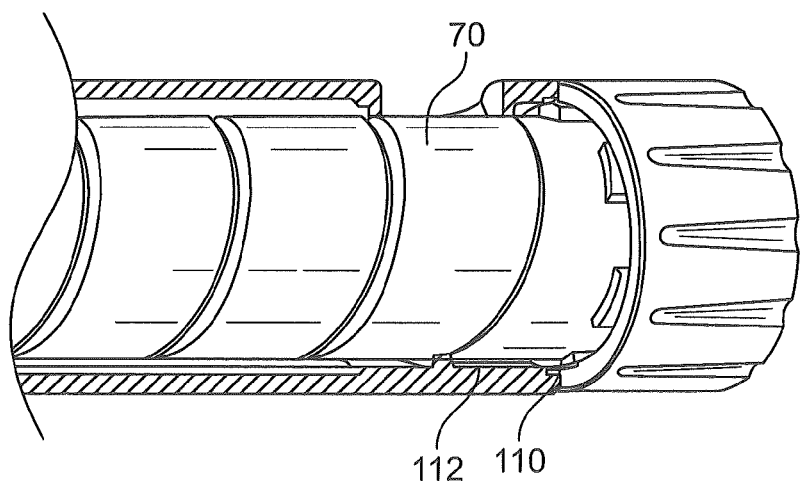
FIG. 14 shows a partially cut-away view of the pen-type injector of FIG. 1 in one of the first, third or fifth positions.

The longitudinal axial movement of the drive sleeve 30 causes the piston rod 20 to rotate though the opening 18 in the insert 16, thereby to advance the piston 10 in the cartridge 8. Once the dialed dose has been dispensed, the dose dial sleeve 70 is prevented from further rotation by contact of a plurality of members 110 (FIG. 14) extending from the dose dial grip 76 with a corresponding plurality of stops 112 formed in the main housing 4 (FIGS. 15 and 16). In the illustrated embodiment, the members 110 extend axially from the dose dial grip 76 and have an inclined end surface. The zero dose position is determined by the abutment of one of the axially extending edges of the members 110 with a corresponding stop 112.

The invention claimed is:
1. A housing part for a medication dispensing apparatus, said housing part comprising:
    a main housing, said main housing extending from a distal end to a proximal end;
    a dose dial sleeve positioned within said housing, said dose dial sleeve comprising a helical groove configured to engage a threading provided by said main housing;
    a dose knob disposed near a proximal end of said dose dial sleeve;

a piston rod provided within said housing, said piston rod is non-rotatable during a dose setting step relative to said main housing;

a driver extending along a portion of said piston rod, said driver comprising an internal threading near a distal portion of said driver, said internal threading adapted to engage an external thread of said piston rod; and, a tubular clutch located adjacent a distal end of said dose knob, said tubular clutch operatively coupled to said dose knob, wherein said dose dial sleeve extends circumferentially around at least a portion of said tubular clutch.

2. The housing part of claim 1, wherein said tubular clutch is directly coupled to said dose knob.

3. The housing part of claim 1, wherein said main housing comprises a window through which at least a portion of an outer surface of said dose dial sleeve may be viewable.

4. The housing part of claim 3, wherein said window is located near a proximal end of said main housing and near a helical rib provided on an inner surface of said outer housing.

5. The housing part of claim 1, wherein said driver comprises a cylindrical shape.

6. The housing part of claim 1, wherein said dose knob extends circumferentially around at least a portion of said tubular clutch.

7. The housing part of claim 1, wherein during a dose dispensing step, said dose knob is activated in a distal direction and said tubular clutch disengages such that said dose dial sleeve rotates back towards said proximal end of said main housing.

8. The housing part of claim 7, wherein during said dose dispensing step, said dose dial sleeve and said tubular clutch rotate together.

9. The housing part of claim 1, further comprising
a container housing operatively coupled to said main housing, said container housing comprising a fluid container,
wherein said fluid container defines a medicament filled reservoir with a movable plunger at a proximal end and an outlet at a distal end,
said plunger movable by said piston rod to be advanced toward an outlet of said fluid container when said piston rod is moved distally, wherein
during a dose dispensing step, said driver advances axially in a distal direction relative to said main housing, and
said driver advances said piston rod in said distal direction so as to dispense said medicament from said outlet at said distal end of said fluid container.

10. The housing part of claim 1, wherein said dose setting knob is coupled in part by said clutch to said dose dial sleeve so as to prevent relative movement between said dose setting knob and said dose dial sleeve during a dose setting step.

11. The housing part of claim 1, wherein said dose setting knob is partially secured to said dose dial sleeve so as to allow relative movement between said dose setting knob and said dose dial sleeve during a dose dispensing step.

12. The housing part of claim 1, wherein said driver comprises at least one flange.

13. The housing part of claim 12, wherein said at least one flange is located near a distal portion of said driver.

14. The housing part of claim 1, further comprising a clicker, said clicker providing at least an audible feedback to a user when said dose knob is rotated.

15. The housing part of claim 14, wherein said clicker provides tactile feedback to a user when said dose knob is rotated.

16. The housing part of claim 14, wherein said clicker provides audible feedback when said dose knob is rotated in a dose increasing direction.

17. The housing part of claim 14, wherein said clicker provides audible feedback when said dose knob is rotated in a dose decreasing direction.

18. The housing part of claim 14, wherein said clicker comprises,
at least one flexible arm, said flexible arm comprising at least one tooth member, and
at least one spline,
wherein when said dose knob is rotated, said at least one flexible arm deforms and drags said tooth member over said at least one spline so as to provide said audible feedback.

19. The housing part of claim 14, wherein said clicker is disposed between said clutch and a proximal end of said piston rod.

20. The housing part of claim 14, wherein
said clicker generally comprises a cylindrical shape having a first and a second end, and
said cylindrical shape is provided at said first end with at least one flexible extending arm.

21. The housing part of claim 1, wherein
said tubular clutch comprises a plurality of teeth formed near an end of said tubular clutch,
said plurality of teeth remaining meshed during a dose setting step, and
said plurality of teeth becoming unmeshed during a dose dispensing step.

22. The housing part of claim 21, wherein said plurality of teeth comprise a plurality of dog teeth.

23. The housing part of claim 1, wherein said piston rod comprises a generally circular cross section.

24. The housing part of claim 1 wherein said external thread of said piston rod comprises a part thread.

25. The housing part of claim 1,
wherein said piston rod comprises a first thread and a second thread, and
wherein at least one of said first or said second thread comprises at least one part threads rather than a complete thread.

26. The housing part of claim 1, wherein said dose dial sleeve is provided outside said tubular clutch and radially inward of said main housing.

27. The housing part of claim 1, wherein said main housing further comprises a helical rib, said helical rib adapted to be seated in said helical groove provided along an outer surface of said dose dial sleeve.

28. The housing part of claim 27, wherein said helical rib extends for at least a single sweep of said inner surface of said main housing.

29. The housing part of claim 27, wherein said helical rib comprises a single start helical rib.

30. The housing part of claim 1, wherein said dose dial sleeve comprises at least one radial stop, said radial stop positioned near an end of said helical groove.

31. The housing part of claim 30, wherein when said dose dial sleeve is rotated to set a maximum dose of said medication dispensing apparatus, said radial stop near said end of said helical groove abuts an end of said threading provided on said inner surface of said main housing and thereby prevents rotation of said dose dial sleeve.

32. The housing part of claim 30, wherein said radial stop is positioned near a distal end of said helical groove.

33. The housing part of claim 1, wherein if a user inadvertently dials said dose knob in one direction beyond a desired dose, said dose knob may be rotated in a second direction so as to allow said dialed dose to be reduced.

34. The housing part of claim 1, wherein, to dispense a set dose, said dose knob is activated, and wherein activation of said dose knob disengages said tubular clutch in an axially direction with respect to said dose dial sleeve.

35. The housing part of claim 1, further comprising
a container housing operatively coupled to said main housing, said container housing comprising a fluid container, wherein said fluid container defines a medicament filled reservoir with a movable plunger at a proximal end and an outlet at a distal end,
said plunger movable by said piston rod to be advanced toward an outlet of said fluid container when said piston rod is moved distally, wherein said housing part is configured such that a user is prevented from dialing a dose of medicament greater than said medicament remaining in said fluid container.

36. The housing part of claim 1, wherein said housing part and said container comprises a disposable device.

37. The housing part of claim 1, wherein said housing part and said container comprises a re-usable device.

38. The housing part of claim 1, further comprising an insert, said insert provided at a distal end of the main housing, said insert secured against rotation.

39. The housing part of claim 1, further comprising an insert, said insert provided at a distal end of the main housing, and said insert secured against longitudinal motion.

40. The housing part of claim 39, wherein said insert comprises an opening extending therethrough, such that said piston rod is configured to extend through said opening.

41. The housing part of claim 40, wherein said opening comprises a threaded opening, and wherein during a dose dispense step, an external thread of said piston rod threadingly engages said threaded opening so that said piston rod rotates during a dose dispense step.

42. The housing part of claim 1, wherein said helical groove of the dose dial sleeve has a first lead and said internal threading of said driver has a second lead, and wherein said first lead and said second lead are the same.

43. A pen type drug delivery device, said device comprising:
an external housing comprising a threading along a portion of an inner surface of said external housing, said external housing extending from a distal end to a proximal end;
a dialing element positioned within said housing, said dialing element comprising an outer surface extending from a distal end to a proximal end of said dialing element, wherein said outer surface comprises a helical threading that defines a groove configured to engage said threading provided on said inner surface of said external housing;
an actuator disposed about an outer surface of an end of said dialing element near said proximal end of said main housing;
a driver extending along at least a portion of a piston rod, said driver comprising a thread adapted to threadingly engage an external thread of a piston rod; and,
a clutch positioned at least partially within an open proximal end of said dialing element and located adjacent a distal end of said actuator and operatively coupled to said actuator,
wherein said dialing element extends circumferentially around at least a portion of said clutch;
a tubular barrel retainer operatively coupled to said external housing, said tubular barrel retainer comprising a cartridge containing a medicament, said cartridge comprising a reservoir, a piston, a septum, and a cap;
said piston movable by said piston rod to be advanced toward an outlet of said cartridge when said piston rod is moved distally.

44. The pen type drug delivery device of claim 43, wherein said tubular barrel retainer is permanently coupled to said external housing.

45. The pen type drug delivery device of claim 43, wherein said tubular barrel retainer is removably coupled to said external housing.

46. The pen type drug delivery device of claim 43, wherein said pen type drug delivery device comprises a prefilled, variable dose pen type drug delivery device.

47. The pen type drug delivery device of claim 43, wherein said outer surface of said dialing element further comprises dosage indicator markings.

48. The pen type drug delivery device of claim 43, wherein said external housing further comprises a housing window, and wherein said housing window allows said dosage indicator markings to be visible during use of said pen type drug delivery device.

49. The pen type drug delivery device of claim 43, wherein said driver comprises a cylindrical, tube-shaped body.

50. The pen type drug delivery device of claim 43, wherein said clutch comprises a cylindrical clutch.

51. A clutch for use within a pen type drug delivery device, said clutch comprising
a tubular body, said tubular body extending from a distal end to a proximal end; and said distal end of said tubular body having a diameter sized such that said distal end of said tubular body may be positioned within a proximal end of a dial member.

52. The clutch of claim 51, wherein said proximal end of said tubular body is configured to reside within an inner space of a dose knob.

53. The clutch of claim 52, wherein when said dose knob is activated to dispense a dose of a medicament contained within said pen type delivery device, said clutch is moved in a distal direction.

54. The clutch of claim 52, wherein said pen type drug delivery device further comprises
a cartridge containing a medicament, said cartridge comprising a reservoir, a stopper, a septum and a ferrule.

55. The clutch of claim 54, wherein said cartridge comprises a multidose cartridge.

56. The clutch of claim 51, further comprising a plurality of axially extending teeth formed in an interior of a flange of said clutch.

57. The clutch of claim 51, wherein said clutch is positioned within an open proximal end of said dial member and located adjacent a distal end of said dose knob and operatively coupled to said dose knob, and wherein said dial member extends circumferentially around at least a portion of said clutch.

* * * * *